United States Patent
Ikeda et al.

(10) Patent No.: US 8,200,006 B2
(45) Date of Patent: Jun. 12, 2012

(54) IMAGE PROCESSING APPARATUS FOR ANALYSIS OF PATTERN MATCHING FAILURE

(75) Inventors: Mitsuji Ikeda, Hitachinaka (JP); Tatsuya Maeda, Hitachinaka (JP); Osamu Nasu, Hitachinaka (JP); Fumihiro Sasajima, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 171 days.

(21) Appl. No.: 12/434,786

(22) Filed: May 4, 2009

(65) Prior Publication Data
US 2009/0214122 A1 Aug. 27, 2009

Related U.S. Application Data

(63) Continuation of application No. 11/499,805, filed on Aug. 7, 2006, now Pat. No. 7,545,977.

(30) Foreign Application Priority Data

Aug. 8, 2005 (JP) ................. 2005-229800

(51) Int. Cl.
*G09K 9/00* (2006.01)
(52) U.S. Cl. ...................... 382/165; 382/209

(58) Field of Classification Search ............... 382/209, 382/165, 145, 132, 118
See application file for complete search history.

(56) References Cited

U.S. PATENT DOCUMENTS

| | | | |
|---|---|---|---|
| 5,805,727 A | 9/1998 | Nakano | |
| 6,627,888 B2 | 9/2003 | Yamaguchi et al. | |
| 6,944,331 B2 * | 9/2005 | Schmidt et al. | 382/165 |
| 7,224,823 B2 | 5/2007 | Hayata et al. | |
| 2002/0114520 A1 * | 8/2002 | Sugawara | 382/209 |
| 2003/0202703 A1 | 10/2003 | Ogi | |
| 2004/0120009 A1 | 6/2004 | White et al. | |
| 2004/0146194 A1 | 7/2004 | Ichikawa et al. | |

FOREIGN PATENT DOCUMENTS

| | | |
|---|---|---|
| JP | 09-245709 | 9/1997 |
| JP | 11-085907 | 3/1999 |
| JP | 11-204621 | 7/1999 |
| JP | 2003-317082 A | 11/2003 |

OTHER PUBLICATIONS

Japanese Office Action dated Jun. 29, 2010 (two (2) pages).

* cited by examiner

*Primary Examiner* — Kiet T Nguyen
(74) *Attorney, Agent, or Firm* — Crowell & Moring LLP (57) ABSTRACT

Information indicating the reason for a failure of template matching is provided. Difference information between a first image, which is referred to as a template, and a third image that is selected by the operator from a second image and that is larger than the template is displayed.

12 Claims, 11 Drawing Sheets

IMAGE PROCESSING APPARATUS FOR ANALYSIS OF PATTERN MATCHING FAILURE

CROSS REFERENCE TO RELATED APPLICATION

This application is a continuing application of U.S. application Ser. No. 11/499,805, filed Aug. 27, 2006, which claims priority under 35 U.S.C. §19 to Japanese Patent Application No. 2005-229800, filed Aug. 8, 2005, the entire disclosure of which are herein expressly incorporated by reference.

BACKGROUND OF THE INVENTION

1. Field of the Invention

The present invention relates to an apparatus for inspecting semiconductor processing apparatuses, and to an image processing device built inside such inspecting apparatus.

2. Background Art

Semiconductor inspecting apparatuses are used for measuring the pattern width at a predetermined inspection position on a circuit pattern formed on a semiconductor wafer, for example, or for conducting an inspection for defective etching or the like. Such measurement or inspection involves pattern matching with the use of a pre-registered pattern image (template image), whereby the field of vision of the inspection apparatus is aligned with an inspection position. Specifically, a characteristic pattern near the inspection position is looked for by pattern matching using the template image, and then a position spaced apart from the characteristic pattern in a known direction by a known distance is defined as the inspection position (see JP Patent Publication (Kokai) No. 11-204621 A (1999), for example).

JP Patent Publication (Kokai) No. 11-85907 A (1999) discloses an image processing device that displays differential data between a process target image and a pattern image so as to facilitate the visual detection of pattern defects on an image. This device conducts pattern matching between each region of the process target image and the pattern image. Depending on the result of the pattern matching, a predetermined process target image region is selected, and similarity difference between the selected process target image region and the pattern image is computed. The thus computed similarity difference data is displayed on a data display unit.

Patent Document 1: JP Patent Publication (Kokai) No. 11-204621 A (1999)
Patent Document 2: JP Patent Publication (Kokai) No. 11-85907 A (1999)

SUMMARY OF THE INVENTION

Sometimes, semiconductor inspection apparatuses fail to carry out pattern search normally by pattern matching with the use of a template image. As a result, it may become impossible for the apparatus to move its field of vision to a predetermined inspection position on a circuit pattern formed on a semiconductor wafer, thereby failing to conduct a desired inspection. In such a case, it would be useful for achieving higher throughput and for carrying out highly accurate inspection if the cause of the failure for pattern matching using the template image can be found However, in the method disclosed in JP Patent Publication (Kokai) No. 11-85907 A (1999), because the similarity difference that is displayed is that between the image data of a process target image region that is judged to have the highest pattern matching and the pattern image, virtually no information can be obtained regarding the reason for pattern matching failure if any.

It is therefore an object of the invention to provide the operator with information regarding the reason for failure in pattern matching.

The invention provides an image processing device comprising: a first memory means for storing a template image for pattern matching; a second memory means for storing an image of a subject; a display means for displaying the template image and the image of the subject; a region specifying means for specifying a region in the image of the subject that is to be used for the calculation of difference information with respect to the template image; and a computing means for computing the difference information between the region of the image of the subject specified by the region specifying means and the template image, and for displaying the result of computation on the display means.

The region specifying means may include an input means for designating a desired region on the image of the subject displayed on the display means. Also, the region specifying means may include a template matching means, wherein the region in the image of the subject specified by the input means is subjected to template matching using the template image so as to specify a region.

The region specifying means may include a template matching means for carrying out template matching and outputting a plurality of matching candidates with respect to the image of the subject using the template image, and an input means for designating a desired matching candidate from among the plurality of matching candidates outputted by the template matching means. The region specifying means may include means for displaying the template image on the display means in a semitransparent manner, and an input means for moving the template image displayed in a semitransparent manner on the subject image.

In accordance with the invention, detailed information indicating the cause of a failure of pattern matching can be obtained, which makes it easier to analyze a more appropriate algorithm for the image with which pattern matching has failed.

DESCRIPTION OF THE PREFERRED
EMBODIMENTS OF THE INVENTION

In the following, embodiments of the invention will be described with respect to the attached drawings.

Figure 1:
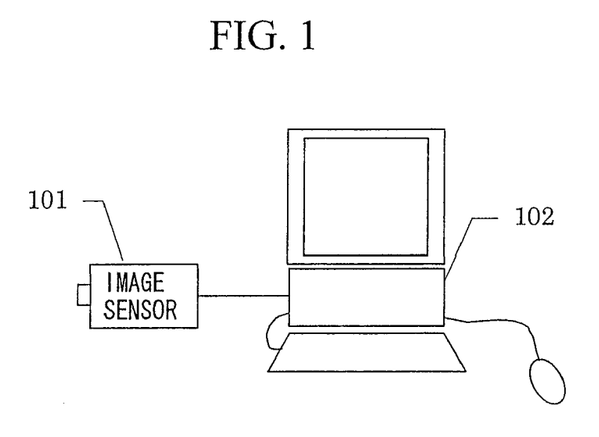
FIG. 1 schematically shows an example of the configuration of an image processing system according to the present invention.

FIG. 1 schematically shows an example of the configuration of an image processing system according to the invention. The illustrated system is composed of an image sensor 101 for acquiring an image of a subject and an image processing device 102. The image sensor 101 captures an image of an inspected object, which is not shown, and converts the image into an electric signal. The image processing device 102 is typically composed of a personal computer and an image processing software. The image captured by the image sensor 101 is transmitted via an image capture board (not shown) to the image processing device 102 where it is processed.

Hereafter, template matching is described, which forms the basis for the present invention. Template matching is a process for searching a larger image for a smaller image referred to as a template. An example of the procedure for template matching using the image processing system configured as shown in FIG. 1 is described with respect to FIG. 2.

Figure 2:
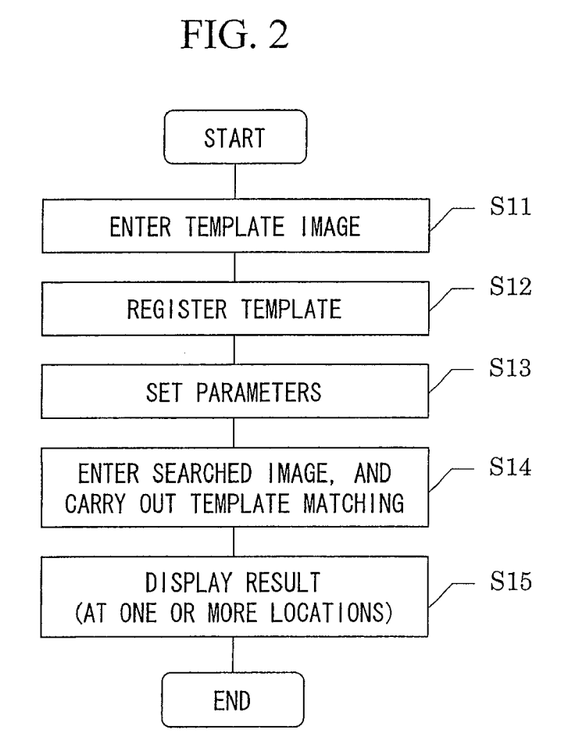
FIG. 2 shows an example of the template matching procedure.

First, an image for a template is entered (S11). The image may be entered via the image sensor 101 or from a database (not shown). Or it may be created on a personal computer using software. Then, a region for a template is designated on the entered image and registered as a template (S12). Parameters for template matching are set (S13), an image (searched image) on which template matching is to be conducted is entered via the image sensor 101, and then template matching is conducted (S14). Finally, the result of template matching, namely, the coordinates of a position on the searched image with high similarity to the template, is displayed (S15). The aforementioned parameters for template matching provide conditions for template matching. They include, for example, the type of filtering used in a preprocessing, a search target region, and the image sampling rate for internal processing.

Figure 3:
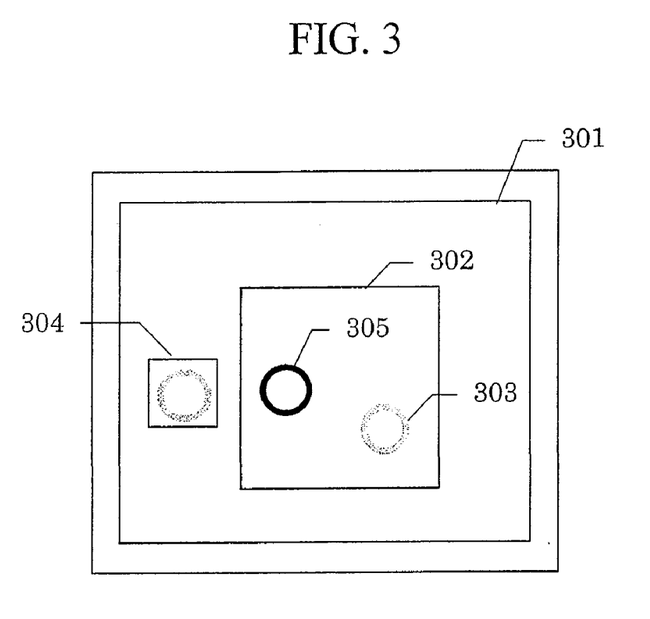
FIG. 3 shows an example of the display screen on which template matching processes are displayed.
Figure 4:
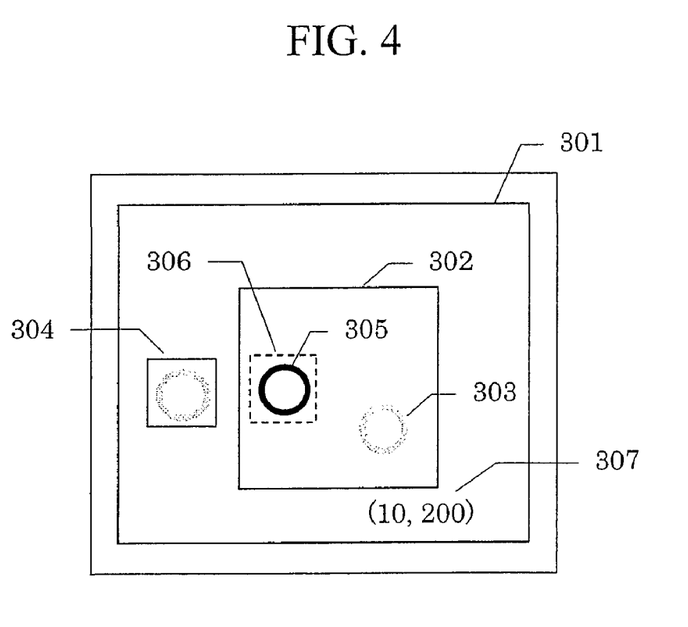
FIG. 4 shows an example of the display screen on which template matching processes are displayed.

FIGS. 3 and 4 show examples of the display screen showing the process of template matching. FIG. 3 shows a state in which a template 304 and a searched image 302 are displayed on a screen 301 of the display unit. FIG. 4 shows the screen after template matching has been carried out in accordance with the procedure shown in FIG. 2. In the screen of FIG. 4, a pattern 305 is detected as a pattern similar the template 304, and a rectangular region 306 and text information 307 are displayed as its coordinates information.

Figure 5:
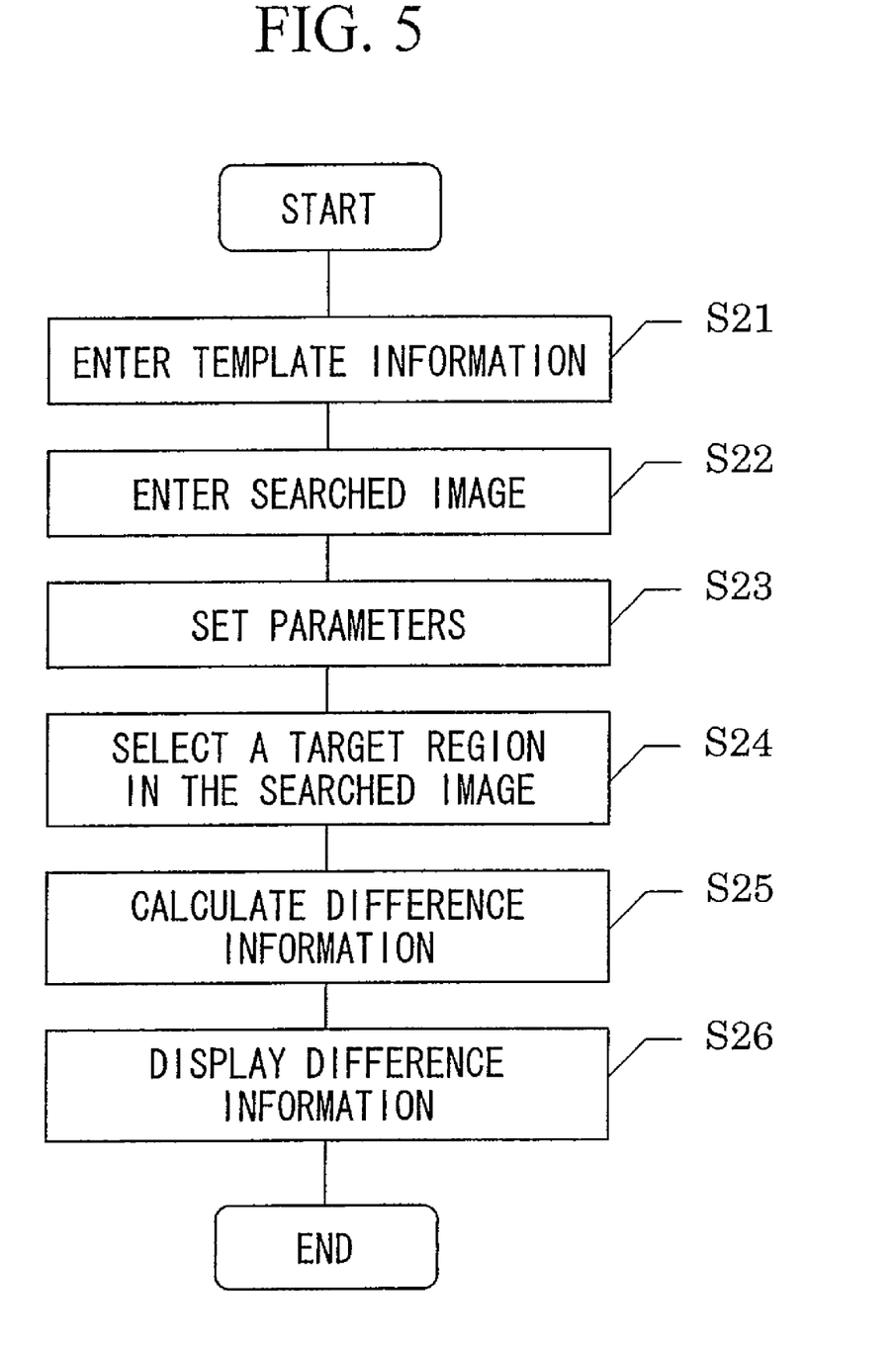
FIG. 5 shows a flowchart of an embodiment of the invention.
Figure 6:
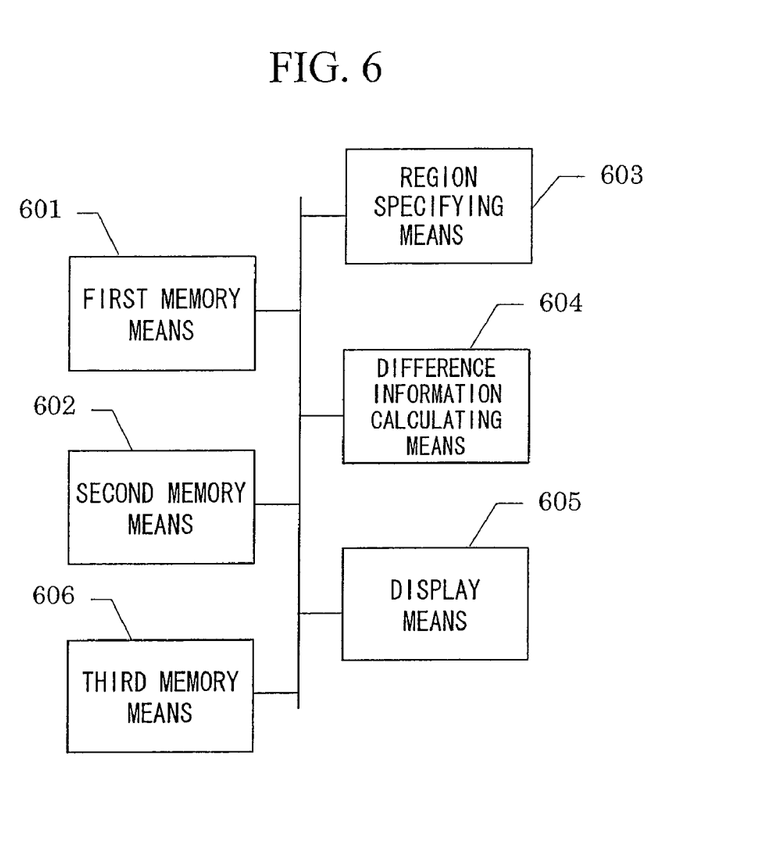
FIG. 6 shows an example of the configuration of an apparatus for carrying out the processes of FIG. 5.

If the result of template matching is not satisfactory to the operator, such as when pattern 305 is detected in FIG. 4 but the actually desired pattern to be detected is pattern 303, a procedure shown in FIG. 5 is carried out as one method for analyzing the cause for the failure to detect pattern 303 in template matching. While in FIG. 4 the pattern 305 corresponds to the template, if the screen displays an inspection point that has a specific relative positional relationship with the pattern 305, a tool may be provided whereby the pattern 305 is calculated from the coordinates information regarding the inspection point and the relative positional information and then displayed. FIG. 6 shows an example of the configuration of an apparatus for conducting the process shown in FIG. 5. The example shown in FIG. 6 includes a first memory means 601 for storing a template, a second memory means 602 for storing a searched image, a region specifying means 603 for specifying a pattern region that the operator wishes to detect in the searched image, a difference information calculating means 604 for calculating difference information between a region of the searched image specified by the region specifying means 603 and the template, a display means 605 for displaying the calculated difference information, and a third memory means 606 for storing parameters. The first memory means 601, the second memory means 602, and the third memory means 606 can be provided by the memories in a personal computer of which the image processing device 102 is formed. The region specifying means 603 may be provided by input means attached to the personal computer, such as a mouse and a keyboard, or by a combination of such input means with an image processing means. The difference information calculating means 604 may be provided by image processing software incorporated in the image processing device 102.

Referring back to FIG. 5, first the template information used for the aforementioned template matching is entered with the input means (S21) and stored in the first memory means 601. The template information herein refers to sufficient information related to the template for conducting the aforementioned template matching. Then, the searched image with which the result of template matching has been unsatisfactory is entered with the input means (S22) and stored in the second memory means 602. Also, the parameters with which the result of template matching has been unsatisfactory are set in the third memory means 606 (S23). The reason for setting the parameters with which the result of template matching has been unsatisfactory is in order to reproduce the template matching process that led to the unsatisfactory result of template matching. Examples of the parameters include the aforementioned type of filtering used in preprocessing, the search target region, and the image sampling rate in internal processing. The parameters may be entered via an execution procedure file (recipe) at the time when template matching was conducted. The order of the aforementioned steps 21, 22, and 23 may be changed.

Thereafter, a region that the operator judges to be closest to the template is selected from the searched image, using the region specifying means 603 (S24). The operation by the region specifying means 603 may involve displaying the searched image on the display means 605 and superposing a region designated with the mouse or other input device on the searched image, so as to designate a region directly. Alternatively, the designation may be made by the method shown in FIGS. 7 to 9 because it is difficult to carry out the designation on a pixel or sub-pixel unit basis without positioning error.

Figure 7:
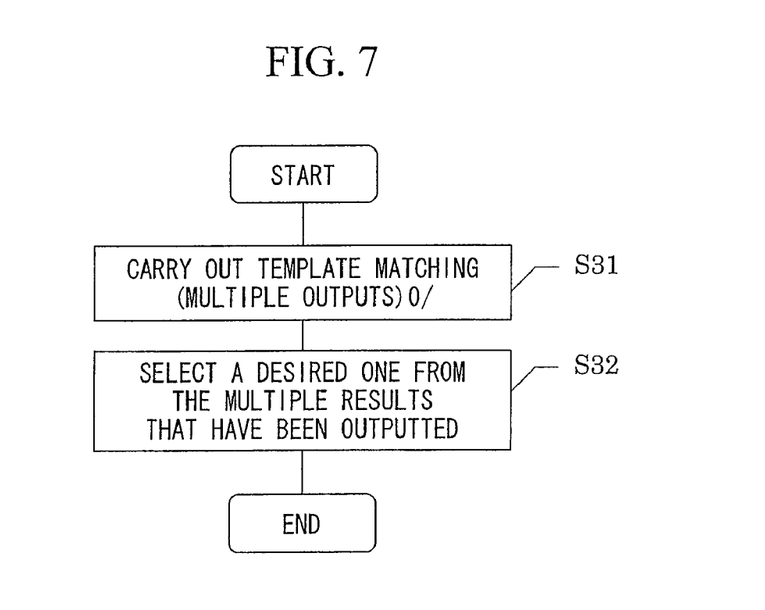
FIG. 7 shows a flowchart of an example of a target region selecting method.
Figure 10:
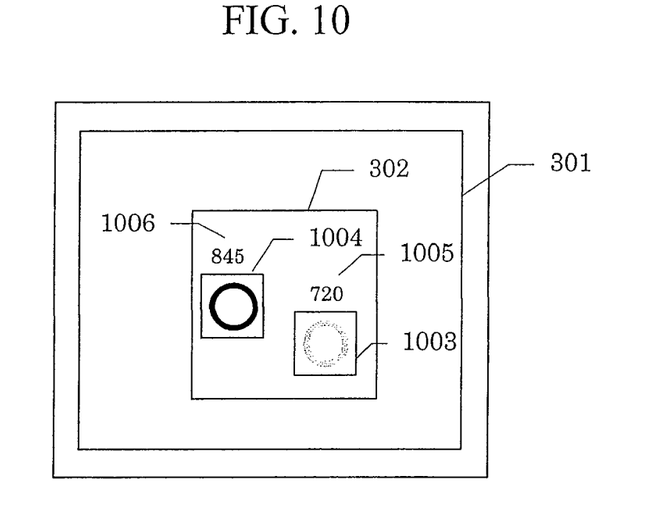
FIG. 10 shows an example of the display screen on which the process of FIG. 7 is displayed.

FIG. 7 shows an example of a method for carrying out step 24 of FIG. 5. This method is based on the same algorithm as that for the template matching in step 14 of FIG. 2. The present method, however, is different in that a process is carried out whereby not just one but a plurality of similarity candidates are outputted (S31). After a plurality of regions similar to the template are outputted, an appropriate one of the regions is selected (S32). An example of the display of a plurality of candidates is shown in FIG. 10, which shows, as candidates for the result of a template matching process, a rectangular region 1003 and its similarity 1005, and a rectangular region 1004 and its similarity 1006. Examples of the method for outputting a plurality of candidates include a method whereby a plurality of candidates with high similarity are selected during the template matching process, and then a predetermined number of candidates are outputted in order of decreasing similarity, and a method whereby all of the candidates having similarity values exceeding a predetermined value are outputted. These methods may be combined.

Figure 11:
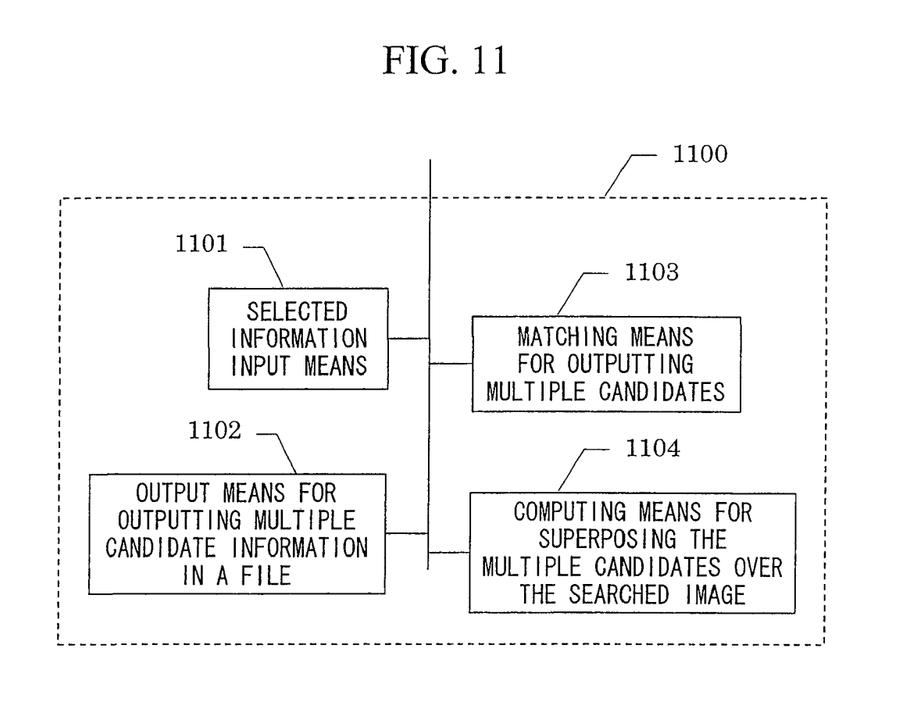
FIG. 11 shows an example of a region specifying means.

FIG. 11 shows an example of the configuration of the region specifying means for realizing the method of FIG. 7. A broken line portion 1100 in FIG. 11 corresponds to the region specifying means. In the region specifying means 1100, a pattern matching process is carried out between the template stored in the first memory means 601 and the searched image stored in the second memory means 602, using the matching means 1103 and based on the parameters stored in the third memory means 606, whereby a plurality of candidates are outputted. The candidates as the results of processing are superposed on the searched image by the computing means 1104. The thus rendered image is displayed on the display means 605. Further, the information about the multiple candidates is outputted in a file by the output means 1102. Of the multiple candidates displayed on the display means 605, a desired one is designated with the input means 1101. Of the constituent elements of the region specifying means 1100 shown, the input means 1101 may be realized with the mouse or keyboard, for example. The rest of the means may be realized with image processing software incorporated in the image processing device 102.

Figure 8:
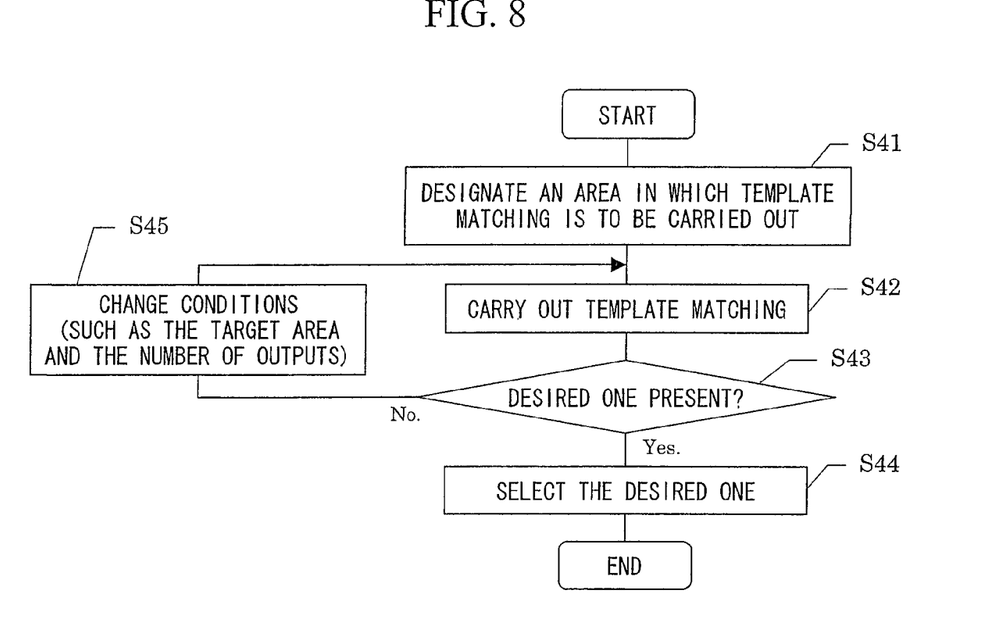
FIG. 8 shows a flowchart of another example of the target region selecting method.

FIG. 8 shows another example of the method for carrying out step 24 of FIG. 5. In this method, an area that includes the region in the searched image that the operator judges to be closest to the template is designated (S41), template matching is conducted only within such area (S42), and then a target region is established (S43, S44). If the desired pattern is not selected, the conditions regarding the target area or the parameters are changed (S45), and then template matching is repeated (S42).

Figure 12:
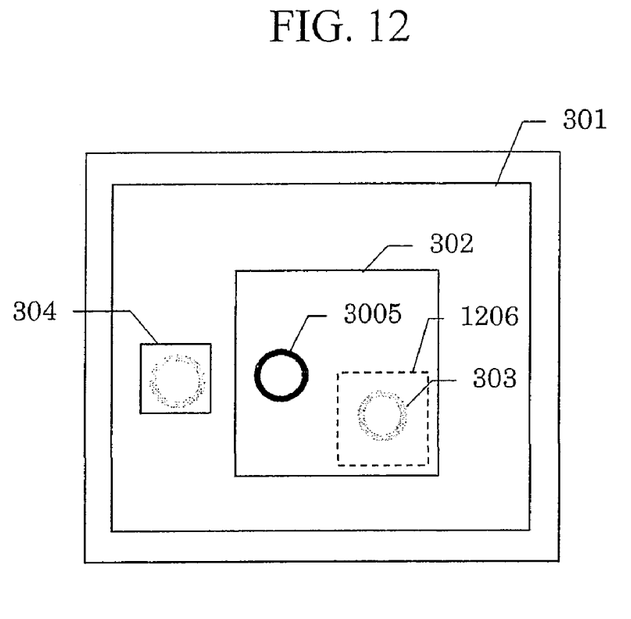
FIG. 12 shows an example of the display screen on which the process of FIG. 8 is displayed.
Figure 13:
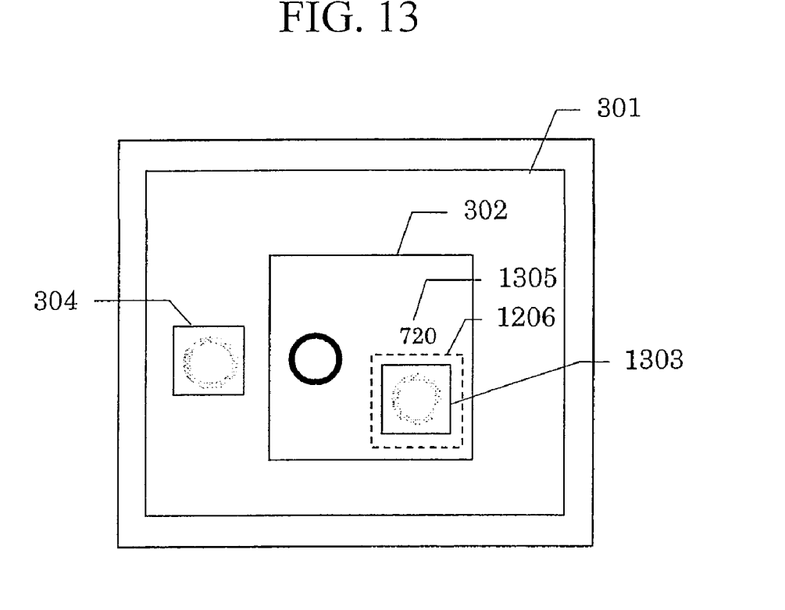
FIG. 13 shows an example of the display screen on which the process of FIG. 8 is displayed.

FIG. 12 shows an example of the display screen immediately after the target area has been designated. FIG. 13 shows an example of the display screen immediately after carrying out template matching. A rectangle 1206 indicated by a broken line in FIG. 12 indicates the designated target region, numeral 1303 in FIG. 13 designates a searched region, and numeral 1305 shows the similarity.

Figure 14:
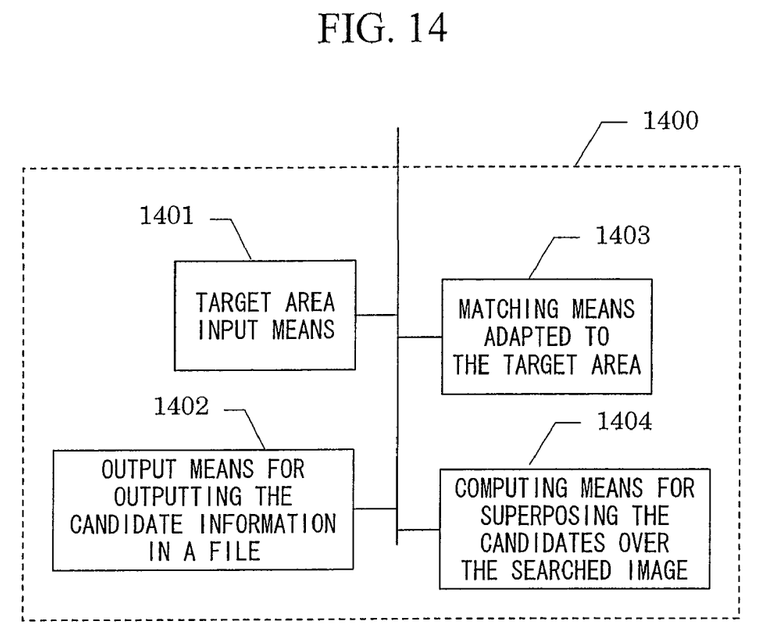
FIG. 14 shows an example of a region specifying means.

FIG. 14 shows an example of the configuration of the region specifying means for carrying out the process of FIG. 8. A portion 1400 enclosed by a broken line 1400 in FIG. 14 corresponds to the region specifying means. In the region specifying means 1400, a pattern matching process is conducted by the matching means 1403 between the template stored in the first memory means 601 and the searched image stored in the second memory means 602, based on the parameters stored in the third memory means 606 and the matching target area entered via the target area input means 1401, whereby candidates as processing results are superposed on the searched image by a computing means 1404. The image thus rendered on the searched image is displayed on the display means 605. Also, candidate information is outputted in a file by the output means 1402. Of the constituent elements of the region specifying means 1400 as shown, the target area input means 1401 may be realized with the mouse or keyboard, for example, and the rest of the means may be realized with image processing software incorporated in the image processing device 102.

Figure 15:
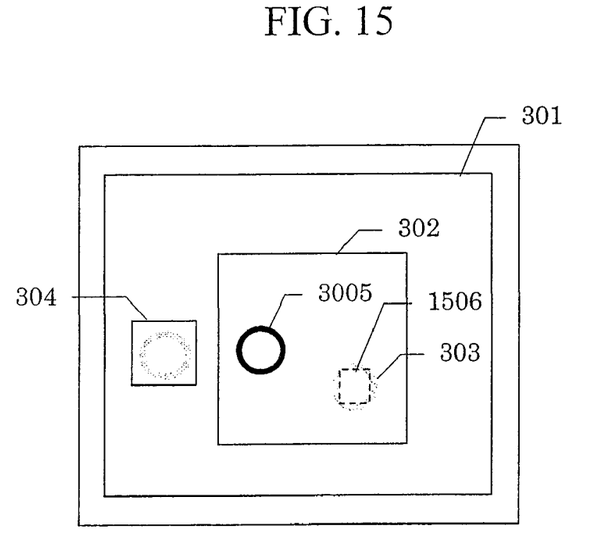
FIG. 15 shows an example of the display screen on which the process of FIG. 8 is displayed.

For the designation of the area in which template matching is conducted, a target region may be established by, as shown in FIG. 15, designating an area near a region that the operator judges to be closest to the template, or an area within a region that the operator judges to be closest to the template (1506), and then carrying out template matching only in the larger area including the area near or within such region.

Figure 9:
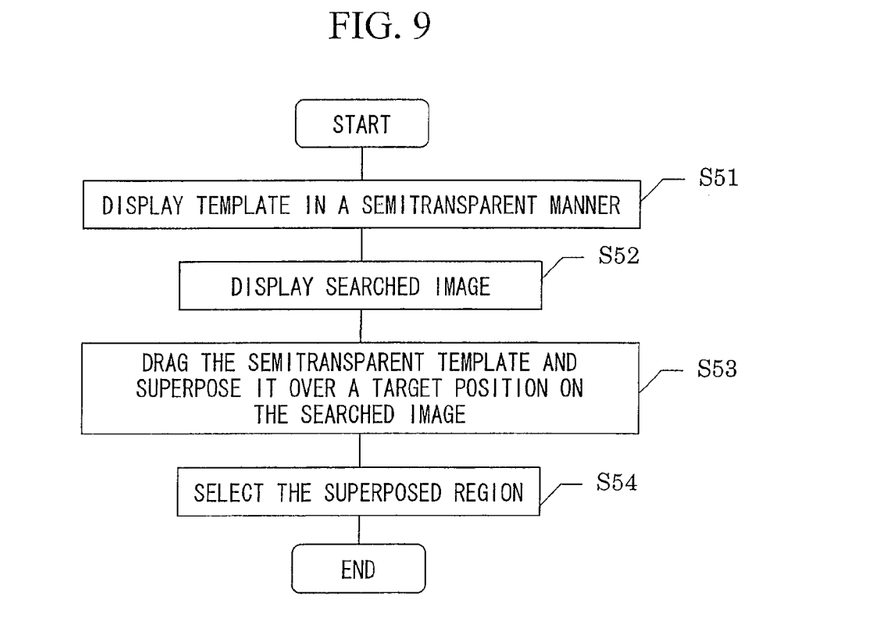
FIG. 9 shows a flowchart of another example of the target region selecting method.
Figure 16:
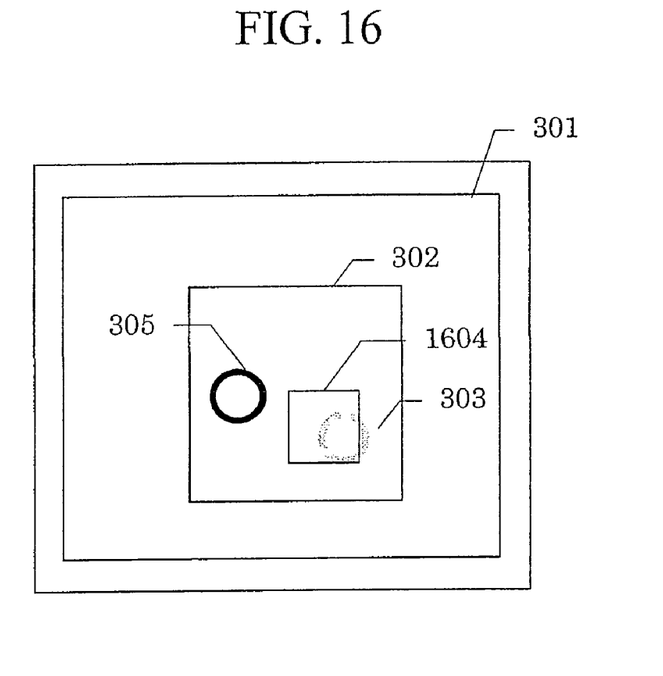
FIG. 16 shows an example of the display screen on which the process of FIG. 9 is displayed.

FIG. 9 shows another example of the method for carrying out step 24 of FIG. 5. This method involves rendering the template semitransparent and dragging it over a region that the operator judges to be closest to the template in the searched image, thereby specifying the target region. First, the template is displayed in a semitransparent manner, (S51), and a searched screen is displayed (S52). Then, the semitransparent template is dragged on the screen and superposed on a target position on the searched screen (S53). The superposed region is then selected (S54). FIG. 16 shows how the operation proceeds on the display screen. Numeral 301 designates the display screen, on which the operator moves the semitransparent template 1604 so as to superpose it on the target region 303 on the searched image 302. Numeral 305 designates a similar pattern. After the region is thus specified by superposing the semitransparent template thereon, template matching may be conducted only in the region near the specified region so as to specify a target region once again.

In another method for providing the coordinates of the target region, the coordinates of a start point of the target region relative to the coordinates of a reference point in the searched image and the size of the region, the coordinates of the start point and an end point of the target region relative to the coordinates of a reference point in the searched image, and the coordinates of a representative point having a relative positional relationship with the template relative to the reference point in the searched image are entered. In the method whereby the coordinates of the representative point having a relative positional relationship with the template relative to the reference point in the searched image are entered, if the actual inspection point is given in terms of its coordinates relative to the template, the target region can be specified by designating the actual inspection point with the input means.

Referring back to FIG. 5, after a region that the operator judges to be closest to the template is selected in the searched image, the difference information between the image of the region and the template is determined using the difference information computing means 604 (S25). While various methods can be contemplated for the calculation of the difference information, desirably one that would directly express the difference in terms of template matching is used. For example, in a case where, after a particular filtering process is carried out during template matching, similarity is determined by the normalized correlation shown by equation (1) below, a difference image is obtained by implementing the below-indicated equation (2) or (3) on the image that has been subjected to the same filtering process as carried out during template matching. In addition to such difference image, similarity in terms of template matching may be calculated and displayed.

$$R(u, v) = \frac{\sum_x \sum_y (f(x+u, y+v) - \bar{f}) \times (g(x, y) - \bar{g})}{\sqrt{\sum_x \sum_y (f(x+u, y+v) - \bar{f})^2} \times \sqrt{\sum_x \sum_y (g(x, y) - \bar{g})^2}} \quad (1)$$

R(u,v): Normalized correlation values in an x×y region having a starting point with the coordinates (u, v) in the searched image
f: Image data at each of the coordinates of the searched image
g: Image data at each of the coordinates of the template
$\bar{f}$: Average image data in the x×y region having the staring point with the coordinates (u, v) in the searched image
$\bar{g}$: Average image data in the template $$\text{diff}_{u,v}(i, j) = \left( \frac{f(i+u, j+v) - \bar{f}}{\sum_x \sum_y (f(x+u, y+v) - \bar{f})^2} - \frac{g(i, j) - \bar{g}}{\sum_x \sum_y (g(x, y) - \bar{g})^2} \right)^2 \times k \quad (2)$$

$\text{diff}_{u,v}(i, j)$: Similarity difference at coordinates (i, j) in an x×y region having a starting point with coordinates (u, v) in the searched image
f: Image data at each of the coordinates of the searched image
g: Image data at each of the coordinates of the template
$\bar{f}$: Average image data in an x×y region having a starting point with coordinates (u, v) in the searched image
$\bar{g}$: Average image data in the template
k: Coefficient for preventing values from becoming too small $$\text{diff}_{u,v}(i, j) = \left( \frac{f(i+u, j+v) - \bar{f}}{\sum_x \sum_y (f(x+u, y+v) - \bar{f})^2} - \frac{g(i, j) - \bar{g}}{\sum_x \sum_y (g(x, y) - \bar{g})^2} \right) \times k \quad (3)$$

Figure 17:
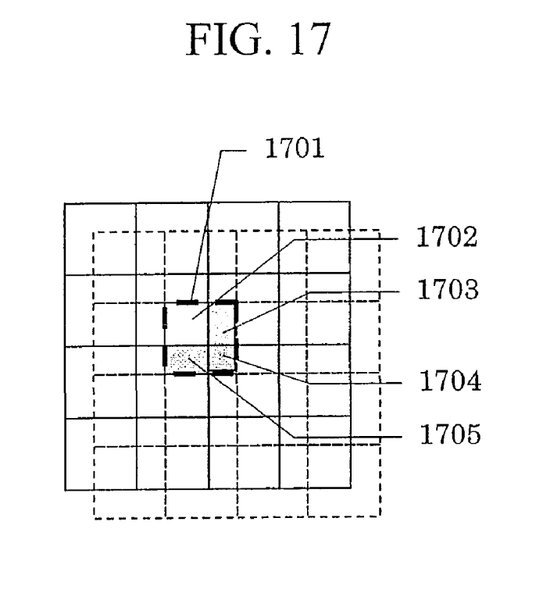
FIG. 17 shows an example of a method for calculating an interpolated image.

$\text{diff}_{u,v}(i, j)$: Similarity difference at coordinates (i, j) in an x×y region having a starting point with coordinates (u, v) in the searched image
f: Image data at each of the coordinates of the searched image
g: Image data at each of the coordinates of the template
$\bar{f}$: Average image data in an x×y region having a starting point with coordinates (u, v) in the searched image
$\bar{g}$: Average image data in the template
k: Coefficient for preventing values from becoming too small When determining a difference image by positioning on a sub-pixel, namely, smaller-than-pixel, basis, an interpolated image is produced so as to allow one or both of the images to be positioned on a sub-pixel basis. FIG. 17 shows an example of the method of creating such interpolated image. The value of a pixel 1701 that is displaced by a sub-pixel distance is obtained by weighting the value of the original pixel depending on the areas 1702, 1703, 1704, and 1705 included in the pixel 1701.

Figure 18:
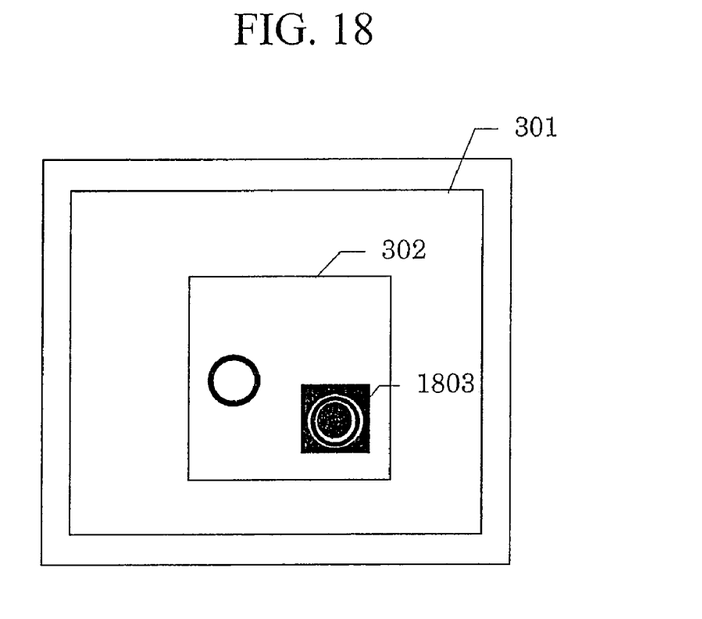
FIG. 18 shows a display screen displaying an example of a difference information display method.
Figure 19:
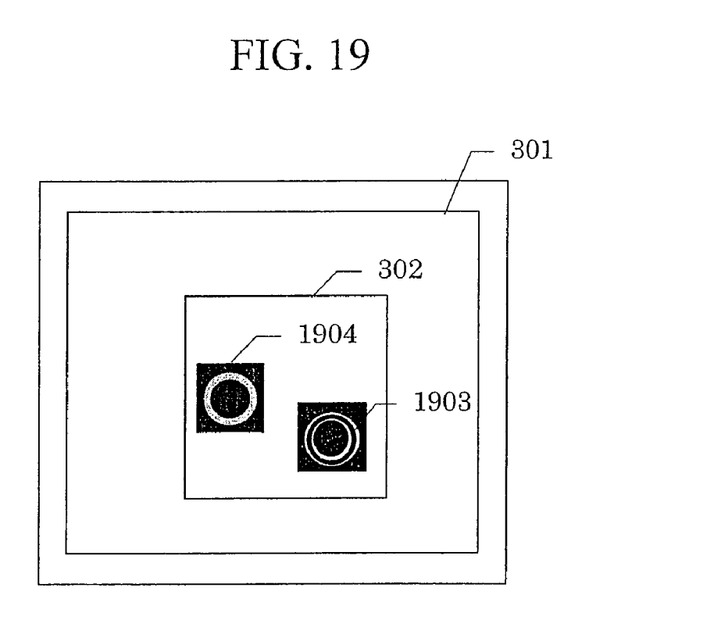
FIG. 19 shows a display screen displaying an example of a difference information display method.

The difference information thus obtained is displayed on the display screen (S26). FIGS. 18 and 19 show methods for such display.

FIG. 18 shows an example where a difference image 1803 calculated by the difference information computing means 604 is displayed on a display means 605 in a region on the searched image 302 that the operator judges to be closest to the template. In FIG. 18, the difference image 1803 expresses the absolute value of the difference using different shades. Alternative methods are also available. Examples include one whereby positive and negative values are expressed in different colors, one whereby positive and negative values are displayed at different times, one whereby the values are binarized using a specific threshold value, and one whereby such threshold value is dynamically varied.

Also, in addition to the difference image, the original image of the template or the searched image, or an image that has been subjected to preprocessing may be substituted manually or automatically. Similarity in terms of template matching may also be displayed.

FIG. 19 shows, in addition to the difference information 1903 between the region that the operator judged to be closest to the template and the template, difference information 1904 between a region detected by template matching to be a most similar region and the template is displayed. The method for displaying the difference image or other information is similar to the case described with respect to FIG. 18.

While FIG. 19 shows a difference image displayed superposed over a relevant region of the searched image, the images may be displayed separately side by side, because the regions might overlap. Alternatively, they may be displayed in the same region and substituted automatically or manually. Further, the difference information 1903 between the region that the operator judged to be closest to the template and the template, and the difference information 1904 between the region that has been detected as being most similar by template matching and the template may be displayed.

The operator analyzes the cause of failure of template matching by visually inspecting such information or having the difference between difference images calculated. For example, in the case of the example shown in FIG. 19, it can be estimated that the difference image 1904 has been evaluated to be highly similar due to the little difference in shape, whereas the difference image 1903 has a large difference due to the difference in shape, so that the operator can make changes, such as making template matching more robust against changes in shape.

Figure 20:
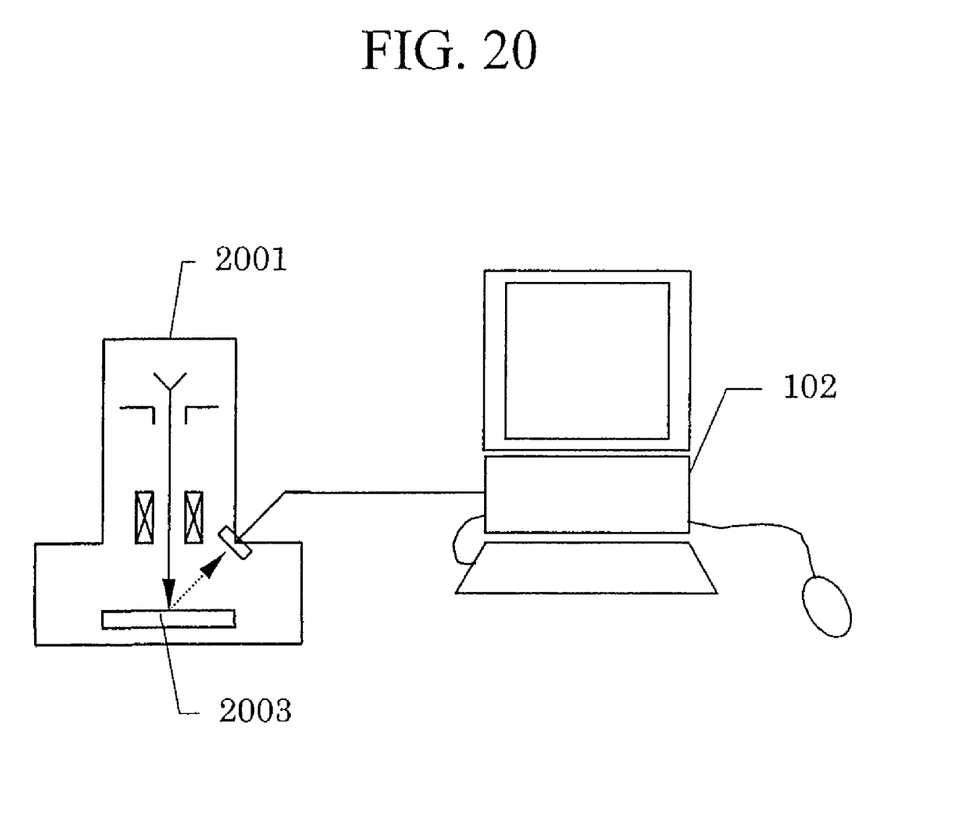
FIG. 20 schematically shows a semiconductor inspection apparatus using an electron microscope.

FIG. 20 shows another embodiment of the invention, which is a semiconductor inspection apparatus involving the use of an electron microscope. This semiconductor inspection apparatus is comprised of an electron microscope 2001 and an image processing device 102. The electron microscope 2001 captures an image of an object placed on a sample mount 2003 and converts it into an electric signal. The image captured by the electron microscope 2001 is transmitted via an image capture board (not shown) to the image processing device 102. The image processing device 102 aligns the position of a sample to be observed and detects defects or foreign matter. The procedure for template matching conducted by the semiconductor inspection apparatus is basically the same as that shown in FIG. 2. The processes that are carried out when the result of template matching has been unsatisfactory to the operator are also the same as those described above.

What is claimed is:

1. An image processing device comprising:
   a memory for storing a template for pattern matching and an image of a subject;
   a display unit for displaying the template and the image of the subject;
   a region specifying means for specifying a region in the image of the subject that is to be used for calculation of difference information with respect to a template image; and
   difference information computing means for computing the difference information between the region in the image of the subject specified by the region specifying means and the template image based on either the equation $$\text{diff}_{u,v}(i, j) = \left( \frac{f(i+u, j+v) - \bar{f}}{\sum_x \sum_y (f(x+u, y+v) - \bar{f})^2} - \frac{g(i, j) - \bar{g}}{\sum_x \sum_y (g(x, y) - \bar{g})^2} \right)^2 \times k,$$

where $\text{diff}_{u,v}(i, j)$ is the difference information at coordinates (i, j) in an x×y region having a starting point with coordinates (u, v) in the searched image, f is image data at each of the coordinates of the searched image, g is image data at each of the coordinates of the template, $\bar{f}$ is average image data in an x×y region having a starting point with coordinates (u, v) in the searched image, $\bar{g}$ is average image data in the template, and k is a coefficient for preventing values from becoming too small, or the equation $$\text{diff}_{u,v}(i, j) = \left( \frac{f(i+u, j+v) - \bar{f}}{\sum_x \sum_y (f(x+u, y+v) - \bar{f})^2} - \frac{g(i, j) - \bar{g}}{\sum_x \sum_y (g(x, y) - \bar{g})^2} \right) \times k,$$

where $\text{diff}_{u,v}(i, j)$ is the difference information at coordinates (i, j) in an x×y region having a starting point with coordinates (u, v) in the searched image, f is image data at each of the coordinates of the searched image, g is image data at each of the coordinates of the template, $\bar{f}$ is average image data in an x×y region having a starting point with coordinates (u, v) in the searched image, $\bar{g}$ is average image data in the template, and k is a coefficient for preventing values from becoming too small, and outputting the difference information for display on the display unit.

2. The image processing device according to claim 1, wherein the region specifying means includes an input unit for designating a desired region on the image of the subject displayed on the display unit.

3. The image processing device according to claim 2, wherein the region specifying means includes a template matching device, wherein the region in the image of the subject specified by the input unit is subjected to template matching using the template image so as to specify a region.

4. The image processing device according to claim 3, wherein the display unit also displays difference information between a region detected as being most similar to the template image by the template matching performed on the subject image and the template image.

5. The image processing device according to claim 1, wherein the region specifying means includes a template matching device for carrying out template matching and outputting a plurality of matching candidates with respect to the image of the subject using the template image, and an input unit for designating a desired matching candidate from among the plurality of matching candidates outputted by the template matching device.

6. The image processing device according to claim 1, wherein the region specifying means displays the template image on the display unit in a semitransparent manner, and an input unit for moving the template image displayed in a semitransparent manner on the subject image.

7. An image processing device comprising:
a memory for storing a template for pattern matching and an image of a subject;
a display unit for displaying the template and the image of the subject;
a region specifying device for specifying an objective area in a searched area of the image that is carried out by the pattern matching; and difference information computing means for computing difference information between the objective area in the image of the subject specified by the region specifying device and a template image based on either the equation $$\text{diff}_{u,v}(i, j) = \left( \frac{f(i+u, j+v) - \bar{f}}{\sum_x \sum_y (f(x+u, y+v) - \bar{f})^2} - \frac{g(i, j) - \bar{g}}{\sum_x \sum_y (g(x, y) - \bar{g})^2} \right)^2 \times k,$$

where $\text{diff}_{u,v}(i, j)$ is the difference information at coordinates (i, j) in an x×y region having a starting point with coordinates (u, v) in the searched image, f is image data at each of the coordinates of the searched image, g is image data at each of the coordinates of the template, $\bar{f}$ is average image data in an x×y region having a starting point with coordinates (u, v) in the searched image, $\bar{g}$ is average image data in the template, and k is a coefficient for preventing values from becoming too small, or the equation $$\text{diff}_{u,v}(i, j) = \left( \frac{f(i+u, j+v) - \bar{f}}{\sum_x \sum_y (f(x+u, y+v) - \bar{f})^2} - \frac{g(i, j) - \bar{g}}{\sum_x \sum_y (g(x, y) - \bar{g})^2} \right) \times k,$$

where $\text{diff}_{u,v}(i, j)$ is the difference information at coordinates (i, j) in an x×y region having a starting point with coordinates (u, y) in the searched image, f is image data at each of the coordinates of the searched image, g is image data at each of the coordinates of the template, $\bar{f}$ is average image data in an x×y region having a starting point with coordinates (u, v) in the searched image, $\bar{g}$ is average image data in the template, and k is a coefficient for preventing values from becoming too small, and outputting the difference information for display on the display unit.

8. The image processing device according to claim 7, wherein the region specifying device includes an input unit for designating a desired region on the image of the subject displayed on the display unit.

9. The image processing device according to claim 8, wherein the region specifying device includes a template matching device, and wherein the region in the image of the subject specified by the input unit is subjected to template matching using the template image so as to specify a region.

10. The image processing device according to claim 9, wherein the display unit also displays difference information between a region detected as being most similar to the template image by the template matching performed on the subject image and the template image.

11. The image processing device according to claim 7, wherein the region specifying device includes a template matching device for carrying out template matching and outputting a plurality of matching candidates with respect to the image of the subject using the template image, and an input unit for designating a desired matching candidate from among the plurality of matching candidates outputted by the template matching device.

12. The image processing device according to claim 7, wherein the region specifying device displays the template image on the display unit in a semitransparent manner, and further comprising an input unit for moving the template image displayed in a semitransparent manner on the subject image.

* * * * *